United States Patent

Boller et al.

[11] 4,058,476
[45] Nov. 15, 1977

[54] LIQUID CRYSTALLINE ISONITRILES

[75] Inventors: Arthur Boller, Binningen; Hanspeter Scherrer, Therwil, both of Switzerland

[73] Assignee: Hoffmann-La Roche Inc., Nutley, N.J.

[21] Appl. No.: 605,788

[22] Filed: Aug. 18, 1975

Related U.S. Application Data

[62] Division of Ser. No. 444,923, Feb. 22, 1974, Pat. No. 3,925,444.

[30] Foreign Application Priority Data

Mar. 2, 1973   Switzerland ............. 3099/73

[51] Int. Cl.² ............. C09K 3/34; G02F 1/13
[52] U.S. Cl. ................. 252/299; 252/408; 350/150; 350/160 LC
[58] Field of Search ........ 252/299, 408; 350/150, 350/160 LC; 23/230 LC; 428/1

[56] References Cited

U.S. PATENT DOCUMENTS

| | | |
|---|---|---|
| 3,499,702 | 3/1970 | Goldmacher et al. ........ 252/299 |
| 3,731,986 | 5/1973 | Fergason ........ 252/299 |
| 3,795,436 | 3/1974 | Boller et al. ........ 252/299 |
| 3,796,479 | 3/1974 | Helfrich et al. ........ 252/299 |
| 3,815,972 | 6/1974 | Hsieh ........ 252/299 |
| 3,881,806 | 5/1975 | Suzuki ........ 252/299 |

FOREIGN PATENT DOCUMENTS

| | | |
|---|---|---|
| 2,306,739 | 8/1973 | Germany ............. 252/299 |
| 2,306,738 | 8/1973 | Germany ............. 252/299 |
| 2,024,269 | 12/1971 | Germany ............. 252/299 |

Primary Examiner—Benjamin R. Padgett
Assistant Examiner—T. S. Gron
Attorney, Agent, or Firm—Samuel L. Welt; Bernard S. Leon; William G. Isgro

[57] ABSTRACT

Liquid crystal substances or compounds of the formula

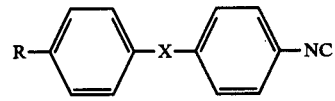

I wherein X is

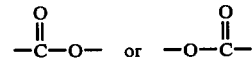

and R is straight-chain alkyl, straight-chain alkoxy, straight-chain alkanoyloxy or p-alkyloxycarbonyloxy, as well as compositions and electro-optical apparatuses containing them, are described.

6 Claims, No Drawings

LIQUID CRYSTALLINE ISONITRILES

This is a division of application Ser. No. 444,923, filed Feb. 22, 1974, now U.S. Pat. No. 3,925,444, issued Dec. 9, 1975.

BRIEF SUMMARY OF THE INVENTION

The invention relates to liquid crystalline compounds of the formula

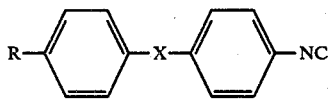   I wherein X is

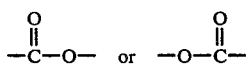

and R is straight-chain alkyl, straight-chain alkoxy, straight-chain alkanoyloxy or p-alkyloxycarbonyloxy.

In another aspect, the invention relates to nematic mixtures for electrooptical uses containing the esters of the invention and to the preparation thereof. In still another aspect, the invention relates to dielectrics for electrooptical uses and to the preparation thereof. In yet another aspect, the invention relates to an optical cell comprising as a liquid crystal means one or more esters of the invention.

DETAILED DESCRIPTION OF THE INVENTION

The invention relates to compounds of the formula

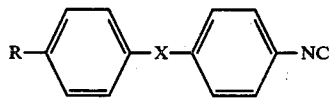   I wherein X is

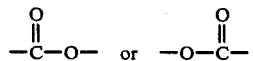

and R is straight-chain alkyl, straight-chain alkoxy, straight-chain alkanoyloxy or p-alkyloxycarbonyloxy, or stated another way, the invention relates to compounds of the formulas

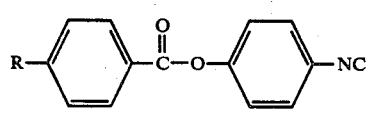   Ia and

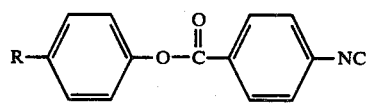   Ib wherein R is as described above.

As used herein, the term "straight-chain alkyl" preferably denotes a straight-chain saturated hydrocarbon containing 1-7 carbon atoms, for example, methyl, ethyl, n-propyl, n-butyl, n-pentyl, and the like. The term "straight-chain alkoxy" preferably denotes a straight-chain alkyl ether group in which the alkyl group is as described above, for example, methoxy, ethoxy, n-propoxy, n-pentoxy, and the like. The term "straight-chain alkanoyloxy" preferably denotes a group derived from an aliphatic carboxylic acid of 1-7 carbon atoms, for example, formyloxy, acetoxy, n-propionyloxy, and the like. The term "p-alkyloxycarbonyloxy" preferably denotes a carbonyloxy group wherein alkyl is a straight-chain alkyl as described above.

The compounds of formula I wherein X is

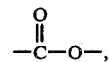

are preferred. Especially preferred are the compounds of formula I wherein R is a straight-chain alkyl.

The compounds of formula I of the invention have, in the liquid crystalline state, a positive anisotropy of the dielectric constants ($\epsilon_\| > \epsilon_\perp$, whereby $\epsilon_\|$ is the dielectric constant along the longitudinal axis of the molecule and $\epsilon_\perp$ is the dielectric constant perpendicular thereto).

In an electric field the nematic liquid crystals of the invention orientate themselves (because $\epsilon_\| > \epsilon_\perp$) with the direction of their largest dielectric constant, that is, with their longitudinal axes, parallel to the field direction. This effect is utilized, inter alia, in the inter-action between embedded molecules and the liquid crystalline molecules (guest-host interaction) described by J. H. Heilmeier and L. A. Zanoni [Applied Physics Letters 13, 91 (1968)]. A further interesting application of the dielectric field orientation is present in the rotation cell discovered by M. Schadt and W. Helfrich [Applied Physics Letters 18, 127 (1971)], as well as in the Kerr cell described in Molecular-Crystals and Liquid Crystals 17, 355 (1972).

The electro-optical rotation cell of Schadt et al., supra, comprises essentially a condenser having transparent electrodes whose dielectric is formed from a nematic substance or liquid crystals having a dielectric constant of $\epsilon_\| > \epsilon_\perp$. The longitudinal axes of the molecules of the liquid crystal are arranged in twisted form between the condenser plates in the fieldless state, the twisting structure being defined by the given wall orientation of the molecules. After the application of an electrical potential to the condenser plates, the molecules adjust themselves with their longitudinal axes in the field direction (i.e., perpendicular to the surface of the plates), whereby linear polarized light is no longer rotated in the dielectric (the liquid crystal is uniaxially perpendicular to the surface of the plates). This effect is reversible and can be used for electrically controlling the optical transmissivity of the condenser.

In such "light rotation cells" it is very desirable to utilize compounds as dielectrics which possess a low melting point and slight viscosity. The compounds previously used for this purpose, e.g., p-[(p-ethyloxybenzylidene)amino]-benzonitrile have the disadvantage of first showing nematic properties at relatively high temperatures so that electro-optical apparatuses provided with such liquid crystals have to be heated and possible thermostatted. Further, said compounds possess a high viscosity which, for example, leads to considerable disadvantages in electro-optical apparatuses in that operation thereof requires relatively large voltages and long response times. Unexpectedly, it has now been discovered that the compounds of formula I of the invention possess liquid crystalline properties which correspond to the foregoing requirements. They exhibit not only the necessary large or strong positive anisotropy of the dielectric constants but also, individually or in the form of their mixtures with one another or with other nematic or non-nematic substances, they are liquid crystalline and exhibit slight viscosity at relatively low temperatures.

An advantage of the compounds of formula I over compounds formerly used for this purpose is their substantially greater stability in view of which they can be handled more conveniently.

The compounds of formula I can be prepared according to the processes hereinafter described. Specifically, by a. dehydrating a compound of the formula

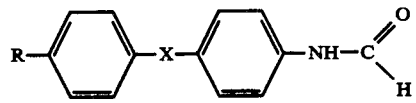

II wherein X is

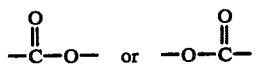

and R is straight-chain alkyl, straight-chain alkoxy, straight-chain alkanoyloxy or p-alkyloxy carbonyloxy, or b. treating a compound of the formula

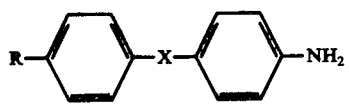

III wherein X and R are as hereinbefore described, with chloroform and a strong base, or c. treating a compound of the formula

IV wherein X and R are as previously described and Hal is fluorine, chlorine, bromine or iodine, with silver cyanide or copper cyanide and, subsequently, with potassium cyanide or d. reducing a compound of the formula

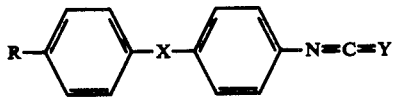

V wherein X and R are as hereinbefore described and Y is oxygen or sulfur, or e. to prepare a compound of formula I wherein X is

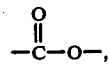

that is, a compound of the formula

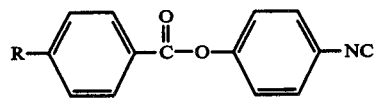

Ia wherein R is as hereinbefore described, reacting a compound of the formula

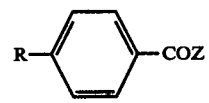

VI wherein R is as previously described, and Z is a leaving group, with p-hydroxybenzoisonitrile, or f. to prepare a compound of formula I wherein X is

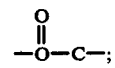

that is, a compound of the formula

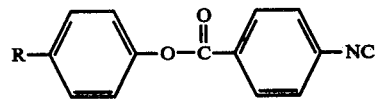

Ib wherein R is as previously described, reacting a compound of the formula

VII wherein Z' is a leaving group, with a compound of the formula

VIII wherein R is as described above.

The term "leaving group" denotes halogen; hydroxy; lower alkoxy of 1 to 7 carbon atoms, preferably methoxy or ethoxy; lower alkylsulfonyloxy of 1 to 7 carbon atoms, preferably mesyloxy; and arylsulfonyloxy, preferably tosyloxy.

Exemplary of the compounds of formula I of the invention, prepared according to the processes described above, are:

p-n-butylbenzoic acid p'-isocyanophenyl ester;
p-n-pentylbenzoic acid p'-isocyanophenyl ester;
p-n-hexylbenzoic acid p'-isocyanophenyl ester;
p-n-heptylbenzoic acid p'-isocyanophenyl ester;
p-n-octylbenzoic acid p'-isocyanophenyl ester;
p-n-butyloxybenzoic acid p'-isocyanophenyl ester;

p-n-pentyloxybenzoic acid p'-isocyanophenyl ester;
p-n-hexyloxybenzoic acid p'-isocyanophenyl ester;
p-n-heptyloxybenzoic acid p'-isocyanophenyl ester;
p-n-octyloxybenzoic acid p'-isocyanophenyl ester;
p-methylcarbonyloxybenzoic acid p'-isocyanophenyl ester;
p-ethylcarbonyloxybenzoic acid p'-isocyanophenyl ester;
p-n-propylcarbonyloxybenzoic acid p'-isocyanophenyl ester;
p-n-butylcarbonyloxybenzoic acid p'-isocyanophenyl ester;
p-n-pentylcarbonyloxybenzoic acid p'-isocyanophenyl ester;
p-n-hexylcarbonyloxybenzoic acid p'-isocyanophenyl ester;
p-n-heptylcarbonyloxybenzoic acid p'-isocyanophenyl ester;
p-n-octylcarbonyloxybenzoic acid p'-isocyanophenyl ester;
p-methyloxycarbonyloxybenzoic acid p'-isocyanophenyl ester;
p-ethyloxycarbonyloxybenzoic acid p'-isocyanophenyl ester;
p-n-propyloxycarbonyloxybenzoic acid p'-isocyanophenyl ester;
p-n-butyloxycarbonyloxybenzoic acid p'-isocyanophenyl ester;
p-n-pentyloxycarbonyloxybenzoic acid p'-isocyanophenyl ester;
p-n-hexyloxycarbonyloxybenzoic acid p'-isocyanophenyl ester;
p-n-heptyloxycarbonyloxybenzoic acid p'-isocyanophenyl ester;
p-n-octyloxycarbonyloxybenzoic acid p'-isocyanophenyl ester;
p-isocyanobenzoic acid p'-n-butylphenyl ester;
p-isocyanobenzoic acid p'-n-pentylphenyl ester;
p-isocyanobenzoic acid p'-n-hexylphenyl ester;
p-isocyanobenzoic acid p'-n-heptylphenyl ester;
p-isocyanobenzoic acid p'-n-octylphenyl ester;
p-isocyanobenzoic acid p'-n-butyloxyphenyl ester;
p-isocyanobenzoic acid p'-n-pentyloxyphenyl ester;
p-isocyanobenzoic acid p'-n-hexyloxyphenyl ester;
p-isocyanobenzoic acid p'-n-heptyloxyphenyl ester;
p-isocyanobenzoic acid p'-n-octyloxyphenyl ester;
p-isocyanophenyl-p'-n-ethylcarbonyloxyphenyl ester;
p-isocyanophenyl-p'-n-propylcarbonyloxyphenyl ester;
p-isocyanophenyl-p'-n-butylcarbonyloxyphenyl ester;
p-isocyanophenyl-p'-n-pentylcarbonyloxyphenyl ester;
p-isocyanophenyl-p'-n-hexylcarbonyloxyphenyl ester;
p-isocyanophenyl-p'-n-heptylcarbonyloxyphenyl ester;
p-isocyanophenyl-p'-n-octylcarbonyloxyphenyl ester;
p-isocyanophenyl-p'-n-ethyloxycarbonyloxyphenyl ester;
p-isocyanophenyl-p'-n-propyloxycarbonyloxyphenyl ester;
p-isocyanophenyl-p'-n-butyloxycarbonyloxyphenyl ester;
p-isocyanophenyl-p'-n-pentyloxycarbonyloxyphenyl ester;
p-isocyanophenyl-p'-n-hexyloxycarbonyloxyphenyl ester;
p-isocyanophenyl-p'-n-heptyloxycarbonyloxyphenyl ester; and
p-isocyanophenyl-p'-n-octyloxycarbonyloxyphenyl ester.

In process embodiment (a) of the invention, a compound of formula II is dehydrated. Conveniently, the dehydration is effected by utilizing an arylsulfonyl chloride in pyridine or quinoline, or by utilizing phosphorus oxychloride in combination with pyridine and potassium t-butylate. Especially preferred as the dehydrating agent, however, is phosgene in the presence of a tertiary amine such as, for example, trimethylamine, triethylamine, tri-n-butylamine, N-methylmorpholine, N,N-diethylaniline, pyridine, quinoline, or the like. The reaction temperature advantageously is in the range of from about 0° to about 150° C., preferably in the range of from about 10° to about 50° C.

The pressure at which the reaction mixture is carried out is not critical. If desired, the process can also be carried out at low temperatures, that is, at temperatures in the range of from about −50° to about −35° C., using thionyl chloride in the presence of dimethylformamide.

In process embodiment (b) of the invention, a compound of formula III is treated with chloroform and a strong base. Suitable strong bases are, for example, potassium t-butylate or a solid alkali metal hydroxide, such as, for example, sodium or potassium hydroxide. The reaction is advantageously carried out in an inert organic solvent such as benzene or toluene. The reaction temperature advantageously is in the range of from about 0° to about 150° C., preferably in the range of from about 50° to about 110° C. The pressure at which the reaction is carried out is not critical.

In process embodiment (c) of the invention, a compound of formula IV forms a complex with silver or copper cyanide, which when treated with potassium cyanide, is converted to a corresponding isonitrile of formula I. Conveniently, the reaction can be carried out without a solvent or in an inert organic solvent, for example, an ether such as diethyl ether or tetrahydrofuran, dimethylformamide, benzene, toluene, cyclohexane or acetonitrile. The reaction is carried out at a temperature below 180° C., preferably at a temperature in the range of from about 80° to about 150° C. The pressure at which the reaction is carried out is not critical.

In process embodiment (d) of the invention, a compound of formula V is reduced. The reduction can be carried out without a solvent or in an inert organic solvent, for example, an ether such as diethyl ether or tetrahydrofuran, dimethylformamide, benzene, toluene, cyclohexane, carbon tetrachloride, petroleum ether or ligroin. The reduction of an isocyanate of formula V is advantageously effected by heating in the presence of triethyl phosphite, triphenyltin hydride or cyclic phosphorus (III) amides, or by irradiation. The reduction of an isothiocyanate of formula V is advantageously effected with triethyl phosphine, triethyl phosphite, copper or triphenyltin hydride, or photolytically. The reaction temperature, as required, advantageously lies in the range of from about 0° to about 180° C., preferably in the range of from about 80° to about 150° C. The pressure at which the reaction is carried out is not critical.

In process embodiments (e) and (f) of the invention, a compound of formula VI or a compound of formula VII is esterified. The esterification is conveniently carried out in an inert organic solvent, for example, an ether such as diethyl ether or tetrahydrofuran, dimethylformamide, benzene, toluene, cyclohexane or carbon tetrachloride.

In the compounds of formulas VI and VII, Z and Z', respectively, are preferably halogen, especially chlorine. In order to bind the hydrogen halide liberated in the reaction, an acid binding agent is conveniently utilized. Suitable acid binding agents are tertiary amines such as pyridines, and the like. The acid binding agent conveniently is utilized in a large excess, so that it can simultaneously serve as a solvent as well as an acid binding agent. The temperature and pressure at which the esterification is carried out are not critical and, in general, atmospheric pressure and temperatures in the range of from about room temperature to about the boiling temperature of the reaction mixture are utilized.

Exemplary of the physical properties of the nematic substances of formula I of the invention are the following:

|  | M.P. (1) | Cl.P. (2) |
|---|---|---|
| p-n-butylbenzoic acid p'-isocyano-phenyl ester | 50.5° | (35.5°)* |
| p-n-pentylbenzoic acid p'-isocyano-phenyl ester | 52.5° | (50.5°)* |
| p-n-hexylbenzoic acid p'-isocyano-phenyl ester | 26.0° – 26.5° | 41.5° |
| p-n-heptylbenzoic acid p'-isocyano-phenyl ester | 37.5° – 38° | 50.5° – 51° |
| p-n-octylbenzoic acid p'-isocyano-phenyl ester | 43° | 48° |
| p-n-heptyloxybenzoic acid p'-isocyanophenyl ester | 62.0° | 79° |
| p-n-pentylcarbonyloxybenzoic acid p'-isocyanophenyl ester | 55.5° | 86° |
| p-n-hexylcarbonyloxybenzoic acid p'-isocyanophenyl ester | 75.7° | 82° |
| p-n-heptylcarbonyloxybenzoic acid p'-isocyanophenyl ester | 56.5° | 85° |
| p-n-butyloxycarbonyloxybenzoic acid p'-isocyanophenyl ester | 72° | 84° |
| p-n-hexyloxycarbonyloxybenzole acid p'-isocyanophenyl ester | 60° – 60.5° | 75.5° |
| p-isocyanobenzoic acid p'-n-hexyl-phenyl ester | 50° | 58° |
| p-isocyanobenzoic acid p'-n-octyl-phenylester | 43.5° | 63.5° |
| p-isocyanobenzoic acid p'-n-hexyl-oxyphenylester | 85.5° | 89.5° |
| p-isocyanobenzoic acid p'-n-heptyl-carbonyloxyphenylester | 74° | 99.5° |
| p-isocyanobenzoic acid p'-n-hexyl-oxycarbonyloxyphenylester | 82.5° – 83.5° | 95° |

*monotrope
(1) melting point
(2) clearing point

The compounds of formula I can be used in the form of mixtures with one another or with other nematic or non-nematic substances. Binary or ternary mixtures can be formed. Especially preferred mixtures comprise those whose composition corresponds to a eutectic.

Thus, in addition to mixtures with one another, the compounds of formula I of the invention can be utilized with other nematic or non-nematic substances, for example, with Schiff's bases of the formula

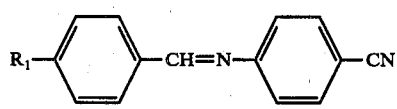

IX wherein $R_1$ is straight-chain alkyl of 2 to 8 carbon atoms, straight-chain alkoxy of 4 to 7 carbon atoms or straight-chain alkanoyloxy of 2 to 8 carbon atoms.

The compounds of formula I of the invention can also be used in the form of mixtures with compounds of the formula

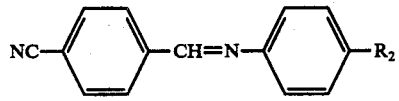

X wherein $R_2$ is straight-chain alkyl of 4 to 7 carbon atoms, or with compounds of the formula

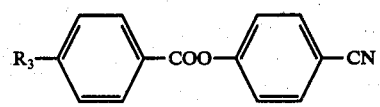

XI wherein $R_3$ is straight-chain alkyl of 4 to 8 carbon atoms or straight-chain alkoxy of 5 to 8 carbon atoms.

The starting materials of formulas III and IV, wherein X is

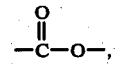

utilized in process embodiments (b) and (c) can be prepared as described hereinafter.

A compound of the formula

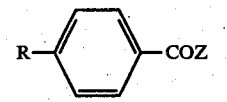

(a)

wherein R is as previously described, is reacted with a compound of the formula

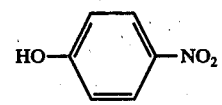

(b)

utilizing known reaction conditions to yield a compound of the formula

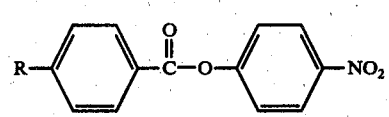

(c)

The compound of formula (c) is reduced utilizing known reaction conditions to yield the starting material of formula III, wherein X is

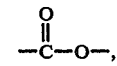

i.e., a compound of the formula

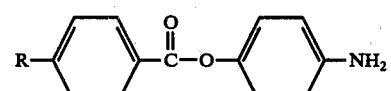

IIIa wherein R is as previously described.

The latter, as required, can be converted utilizing the known Sandmeyer reaction to the starting material of formula IV, wherein X is

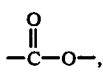

i.e., a compound of the formula

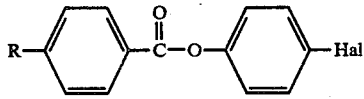
IVa wherein R is as previously described.

The starting materials of formula III and IV, wherein X is

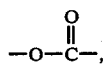

utilized in process embodiments (b) and (c) can be prepared as described hereinafter.

A compound of the formula

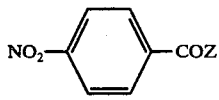
(d)

wherein R is as previously described,
is reacted with a compound of the formula

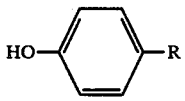
(e)

utilizing known reaction conditions to yield a compound of the formula

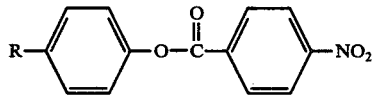
(f)

wherein R is as previously described.

The compound of formula is reduced utilizing known reaction conditions to yield the starting material of formula III, wherein X is

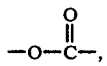

i.e., a compound of the formula

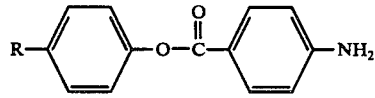
IIIb wherein R is as previously described.

The latter, as required, can be converted utilizing the known Sandmeyer reaction to the starting material of formula IV, wherein X is

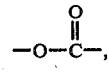

i.e., a compound of the formula

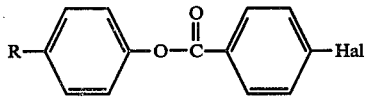
IVa wherein R is as previously described.

The starting materials of formulas (a), (b), (d) and (e) are known compounds or can be prepared according to known procedures.

The starting materials of formula II used in process embodiment (a) can be prepared by the reaction of compounds of formula III with formic acid ethyl ester, with formic acid in benzene with subsequent azeotropic distillation of water, or with a mixture of acetic anhydride/formic acid.

The starting materials of formula V in which Y is oxygen, used in process embodiment (d), can be prepared by the reaction of the corresponding compound of formula III with phosgene. The compounds of formula V in which Y is sulfur, can be prepared by the reaction of the corresponding compound of formula III with thiophosgene or with carbon disulfide and a base via the corresponding diethiocarbamate.

The invention is further illustrated by the following examples. All temperatures are given in degrees Centigrade, unless otherwise specified.

EXAMPLE 1

Preparation of p-n-hexylbenzoic acid p'-isocyanophenyl ester 3.25 G. of p-n-hexylbenzoic acid p'-formamidophenyl ester were dissolved in 50 ml. of methylene chloride and 20 ml. of triethylamine and, at room temperature, treated dropwise with a solution of 1.4 g. of phosgene in 20 ml. of methylene chloride. Subsequently, the mixture was stirred for an additional hour, water was added thereto and then the organic phase was extracted twice with dilute hydrochloric acid. The crude product obtained after being washed neutral, dried and concentrated was chromatographed on 300 g. of silica gel with benzene/1% acetone, whereby there were obtained 1.6 g. of p-n-hexylbenzoic acid p'-isocyanophenyl ester which crystallized in a refrigerator. Crystals having a melting point of 26°–26.5° and a clearing point of 41.5° precipitate from hexane at about −20°.

The starting material p-n-hexylbenzoic acid p'-formamidophenyl ester was prepared as follows:

9.2 G. of N-benzylidene p-aminophenol was treated in 70 ml. of absolute pyridine at 5° with 10.4 g. of p-n-hexylbenzoic acid chloride in 25 ml. of pyridine. The mixture was stirred overnight at room temperature and then poured with stirring onto ice-water. The precipitated product was removed by filtration, washed thoroughly with water, taken up in methylene chloride, dried and concentrated. After recrystallization, there was obtained 12.6 g. of ester having a melting point of 101.5°–103.5° and a clearing point of 114°.

To cleave the Schiff's base, the ester was dissolved in ether. Upon shaking with dilute hydrochloric acid, the hydrochloride salt of the amine precipitated, which was then removed by filtration and washed thoroughly with ether. The hydrochloride salt was decomposed with saturated soda solution and the mixture extracted with ether, whereby there was obtained 9.2 g. of practically pure p-n-hexylbenzoic acid p'-aminophenyl ester. After boiling with formic acid ethyl ester for 24 hours, there was obtained in almost quantitative yield p-n-hexylbenzoic acid p'-formamidophenyl ester which, after recrystallization from ethyl acetate, had a melting point of 126.5°.

In a manner similar to that described above, the following compounds were prepared:

p-n-butylbenzoic acid p'-isocyanophenyl ester having a melting point of 50.5° and a clearing point of 35.5° (monotrope);

p-n-pentylbenzoic acid p'-isocyanophenyl ester having a melting point of 52.5° and a clearing point of 50.5° (monotrope);

p-n-heptylbenzoic acid p'-isocyanophenyl ester having a melting point of 37.5°-38° and a clearing point of 50.5°-51°;

p-n-octylbenzoic acid p'-isocyanophenyl ester having a melting point of 43° and a clearing point of 48°.

p-n-heptyloxybenzoic acid p'-isocyanophenyl ester having a melting point of 62.0° and a clearing point of 79°;

p-n-pentylcarbonyloxybenzoic acid p'-isocyanophenyl ester having a melting point of 55.5° and a clearing point of 86°;

p-n-hexylcarbonyloxybenzoic acid p'-isocyanophenyl ester having a melting point of 75.7° and a clearing point of 85°;

p-n-butyloxycarbonyloxybenzoic acid p'-isocyanophenyl ester having a melting point of 72° and a clearing point of 84°;

p-n-hexyloxycarbonyloxybenzoic acid p'-isocyanophenyl ester having a melting point of 60°-60.5° and a clearing point of 75.5°.

EXAMPLE 2

Preparation of p-n-heptylbenzoic acid p'-isocyanophenyl ester 6.1 G. of p-n-heptylbenzoic acid p'-formamidophenyl ester prepared in accordance with the procedure of Example 1 were dissolved in 40 ml. of dimethylformamide and cooled to −55°. Then, 2.25 g. of thionyl chloride in 5 ml. of dimethylformamide were added dropwise. The resulting mixture was stirred for a few more minutes at the same temperature and then allowed to rise to −45°. At this point, 4 g. of anhydrous soda were added. This mixture was again cooled below −50° and then stirred overnight at room temperature, whereupon the reaction mixture was poured over water and extracted with methylene chloride, and there was finally obtained a mixture of the starting material and of p-n-heptylbenzoic acid p'-isocyanophenyl ester. The p-n-heptylbenzoic acid can be isolated by chromatography on silica gel. Melting point 37.5°-38°, clearing point 50.5°-51°.

EXAMPLE 3

Preparation of p-n-isocyanobenzoic acid p'-hexyloxyphenyl ester 2.2 G. of p-formamidobenzoic acid p'-hexyloxyphenyl ester was dissolved in 100 ml. of methylene chloride and 25 ml. of triethylamine with warming at 40°. With stirring, 0.9 g. of phosgene in 20 ml. of methylene chloride was added thereto. After an additional 2 hours at 40°, the mixture was treated with water and the methylene chloride phase washed with dilute hydrochloric acid and water, dried and concentrated. From 3.2 g. of the resulting product, there was obtained, after chromatography on silica gel with benzene/acetone and recrystallization from hexane, pure p-n-isocyanobenzoic acid p'-hexyloxyphenyl ester having a melting point of 85.5° and a clearing point of 89.5°.

The starting material p-formamidobenzoic acid p'-hexyloxyphenyl ester was prepared as follows:

1.6 G. of p-aminobenzoic acid p'-n-hexyloxyphenyl ester were treated in 75 ml. of toluene with 5 ml. of formic acid (100%) and boiled for 3 hours. The toluene and the formic acid are removed by distillation and, after recrystallization from ethyl acetate, there was obtained 1.7 g. of p-formamidobenzoic acid p'-n-hexyloxyphenyl ester having a melting point of 189.5°.

In a manner similar to that described above, the following compounds were prepared;

p-isocyanobenzoic acid p'-n-hexylphenyl ester having a clearing point of 58° and a melting point of 50°.

p-isocyanobenzoic acid p'-n-octylphenyl ester having a clearing point of 63.5° and a melting point of 43.5°.

p-isocyanobenzoic acid p'-n-heptylcarbonyloxyphenyl ester having a clearing point of 99.5° and a melting point of 74°.

p-isocyanobenzoic acid p'-n-hexyloxycarbonyloxyphenyl ester having a clearing point of 95° and a melting point of 82.5°-83.5°.

We claim:

1. A nematic composition which comprises two or more compounds of the formula

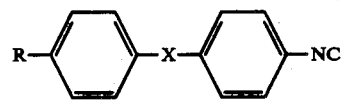

wherein X is

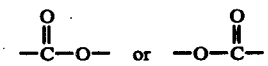

and R is straight-chain alkyl of 1-7 carbon atoms, straight-chain alkoxy of 1-7 carbon atoms, straight-chain alkanoyloxy of 1-7 carbon atoms or p-alkyloxycarbonyloxy wherein the alkyloxy group is straight-chain alkyloxy of 1-7 carbon atoms.

2. A nematic composition which comprises a compound of the formula

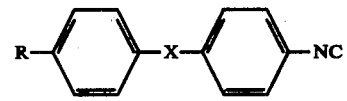

wherein X is

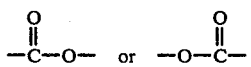

and R is straight-chain alkyl of 1-7 carbon atoms, straight-chain alkoxy of 1-7 carbon atoms, straight-chain alkanoyloxy of 1-7 carbon atoms or p-alkyloxycarbonyloxy wherein the alkyloxy group is straight-chain alkyloxy of 1-7 carbon atoms, or mixtures thereof and one or more nematic compounds having a positive anisotropy.

3. A nematic composition which comprises a compound of the formula

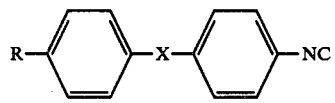

wherein X is

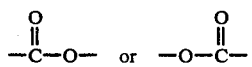

and R is straight-chain alkyl of 1-7 carbon atoms, straight-chain alkoxy of 1-7 carbon atoms, straight-chain alkanoyloxy of 1-7 carbon atoms or p-alkyloxycarboxyloxy wherein the alkyloxy group is straight-chain alkyloxy of 1-7 carbon atoms, or mixtures thereof, and a compound of the formula

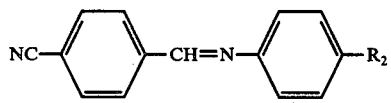

wherein $R_2$ is straight-chain alkyl with 4 to 7 carbon atoms.

4. A nematic composition which comprises a compound of the formula

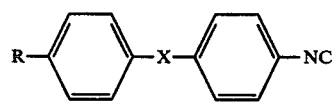

wherein X is

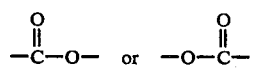

and R is straight-chain alkyl of 1-7 carbon atoms, straight-chain alkoxy of 1-7 carbon atoms, straight-chain alkanoyloxy of 1-7 carbon atoms or p-alkyloxycarbonyloxy wherein the alkoxy group is straight-chain alkyloxy of 1-7 carbon atoms, or mixtures thereof, and a compound of the formula

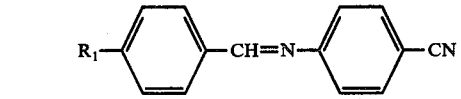

wherein $R_1$ is straight-chain alkyl with 2 to 8 carbon atoms, straight-chain alkoxy with 4 to 7 carbon atoms or straight-chain alkanoyloxy with 2 to 8 carbon atoms.

5. A nematic composition which comprises a compound of the formula

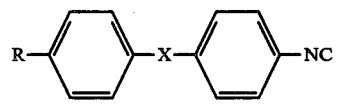

wherein X is

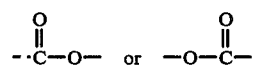

and R is straight-chain alkyl of 1-7 carbon atoms, straight-chain alkoxy of 1-7 carbon atoms, straight-chain alkanoyloxy of 1-7 carbon atoms or p-alkyloxycarbonyloxy wherein the alkyloxy group is straight-chain alkyloxy of 1-7 carbon atoms, or mixtures thereof, and a compound of the formula

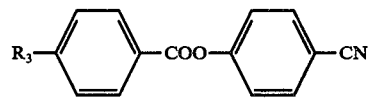

wherein $R_3$ is straight-chain alkyl with 4 to 8 carbon atoms or straight-chain alkoxy with 5 to 8 carbon atoms.

6. A dielectric for electro-optical purposes, which comprises a compound of the formula

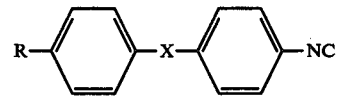

wherein X is

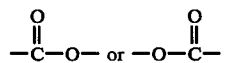

and R is straight-chain alkyl of 1-7 carbon atoms, straight-chain alkoxy of 1-7 carbon atoms, straight-chain alkanoyloxy of 1-7 carbon atoms or p-alkyloxycarbonyloxy wherein the alkyloxy group is straight-chain alkyloxy of 1-7 carbon atoms, or mixtures thereof and one or more nematic compounds having a positive anisotropy.

* * * * *

UNITED STATES PATENT AND TRADEMARK OFFICE
CERTIFICATE OF CORRECTION

PATENT NO. : 4,058,476
DATED : November 15, 1977
INVENTOR(S) : Arthur Boller & Hanspeter Scherrer It is certified that error appears in the above-identified patent and that said Letters Patent are hereby corrected as shown below:

Column 13, claim 4, line 59, "alkoxy group" should be:

alkyloxy group

Signed and Sealed this

Eighteenth Day of April 1978

[SEAL]

Attest:

RUTH C. MASON
Attesting Officer

LUTRELLE F. PARKER
Acting Commissioner of Patents and Trademarks